United States Patent
Wang et al.

(10) Patent No.: US 11,701,081 B2
(45) Date of Patent: Jul. 18, 2023

(54) SYSTEM AND METHOD FOR CONCURRENT VISUALIZATION AND QUANTIFICATION OF BLOOD FLOW USING ULTRASOUND

(71) Applicant: KONINKLIJKE PHILIPS N.V., Eindhoven (NL)

(72) Inventors: Shiying Wang, Melrose, MA (US); Sheng-Wen Huang, Ossining, NY (US); Hua Xie, Cambridge, MA (US); Francois Guy Gerard Marie Vignon, Andover, MA (US); Liang Zhang, Issaquah, WA (US); Keith William Johnson, Lynwood, WA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 205 days.

(21) Appl. No.: 16/498,472

(22) PCT Filed: Mar. 26, 2018

(86) PCT No.: PCT/EP2018/057601
§ 371 (c)(1),
(2) Date: Sep. 27, 2019

(87) PCT Pub. No.: WO2018/177986
PCT Pub. Date: Oct. 4, 2018

(65) Prior Publication Data
US 2021/0106305 A1    Apr. 15, 2021

Related U.S. Application Data

(60) Provisional application No. 62/478,828, filed on Mar. 30, 2017.

(51) Int. Cl.
*A61B 8/06*    (2006.01)
*A61B 8/08*    (2006.01)
(Continued)

(52) U.S. Cl.
CPC ............... *A61B 8/06* (2013.01); *A61B 8/463* (2013.01); *A61B 8/466* (2013.01); *A61B 8/467* (2013.01);
(Continued)

(58) Field of Classification Search
USPC ..................................................... 600/454
See application file for complete search history.

(56) References Cited

U.S. PATENT DOCUMENTS

| 6,443,896 B1 | 9/2002 | Detmer |
| 6,530,885 B1 | 3/2003 | Entrekin et al. |

(Continued)

FOREIGN PATENT DOCUMENTS

| CN | 106102587 A | 11/2016 |
| JP | 2008073279 A | 4/2008 |

(Continued)

OTHER PUBLICATIONS

Angelelli, P., Snare, S. R., Nyrnes, S. A., Bruckner, S., Hauser, H., & Løvstakken, L. (May 2014). Live ultrasound-based particle visualization of blood flow in the heart. In Proceedings of the 30th Spring Conference on Computer Graphics (pp. 13-20). (Year: 2014).*

(Continued)

*Primary Examiner* — Jason M Ip
*Assistant Examiner* — Renee C Langhals

(57) ABSTRACT

A system for visualization and quantification of ultrasound imaging data may include a display unit, and a processor communicatively coupled to the display unit and to an ultrasound imaging apparatus for generating an image from ultrasound data representative of a bodily structure and fluid flowing within the bodily structure. The processor may be configured to generate vector field data corresponding to the fluid flow, wherein the vector field data comprises axial and (Continued)

lateral velocity components of the fluid, extract spatiotemporal information from the vector field data at one or more user-selected points within the image, and cause the display unit to concurrently display the spatiotemporal information at the one or more user-selected points with the image including a graphical representation of the vector field data overlaid on the image, wherein the spatiotemporal information includes at least one of a magnitude and an angle of the fluid flow.

18 Claims, 9 Drawing Sheets

(51) Int. Cl.
    *A61B 8/00*           (2006.01)
    *G16H 30/40*         (2018.01)
    *G16H 50/30*         (2018.01)

(52) U.S. Cl.
    CPC ............ *A61B 8/483* (2013.01); *A61B 8/488* (2013.01); *A61B 8/5223* (2013.01); *G16H 30/40* (2018.01); *G16H 50/30* (2018.01)

(56) References Cited

U.S. PATENT DOCUMENTS

| | | | |
|---|---|---|---|
| 2011/0196237 A1* | 8/2011 | Pelissier | A61B 8/467 |
| | | | 600/454 |
| 2016/0015366 A1 | 1/2016 | Haugaard et al. | |
| 2016/0174931 A1 | 6/2016 | Pelissier et al. | |
| 2018/0064421 A1* | 3/2018 | Moshavegh | A61B 8/5223 |

FOREIGN PATENT DOCUMENTS

| | | |
|---|---|---|
| JP | 2010125203 A | 6/2010 |
| JP | 05063216 B2 | 10/2012 |
| JP | 2015042213 A | 3/2015 |
| JP | 2016153005 A | 8/2016 |
| JP | 2017051424 A | 3/2017 |
| WO | 0027288 A1 | 5/2000 |
| WO | 2012064413 A1 | 5/2012 |
| WO | 2014140657 A1 | 9/2014 |

OTHER PUBLICATIONS

Hansen, K. L., Møller-Sørensen, H., Kjaergaard, J., Jensen, M. B., & Nielsen, M. B. (2016). Intra-operative vector flow imaging using ultrasound of the ascending aorta among 40 patients with normal, stenotic and replaced aortic valves. Ultrasound in medicine & biology, 42(10), 2414-2422. (Year: 2016).*

Evans, D. H., Jensen, J. A., & Nielsen, M. B. (2011). Ultrasonic colour Doppler imaging. Interface Focus, 1(4), 490-502. (Year: 2011).*

Angelelli et al: "Live Ultrasound-Based Particle Visualization of Blood Flow in the Heart"; Proceedings of the 30th Spring Conference on Computer Graphics, 2014, pp. 13-20.

Jensen et al: "Recent Advances in Blood Flow Vector Velocity Imaging", 2011 IEEE International Ultrasonics Symposium, 2011, pp. 262-271.

Evans et al: "Ultrasonic Colour Doppler Imaging"; Interface Focus, vol. 1, No. 4, pp. 490-502, 2011.

Yiu et al: "Vector Projectile Imaging: Time-Resolved Dynamic Visualization of Complex Flow Patterns"; Ultrasound Med. Biol. vol. 40, No. 9, pp. 2295-2309, 2014.

PCT/EP2018/057601 ISR & Written Opinion, dated Jul. 4, 2018, 16 Page Document.

* cited by examiner

SYSTEM AND METHOD FOR CONCURRENT VISUALIZATION AND QUANTIFICATION OF BLOOD FLOW USING ULTRASOUND

CROSS-REFERENCE TO PRIOR APPLICATIONS

This application is the U.S. National Phase application under 35 U.S.C. § 371 of International Application No. PCT/EP2018/057601, filed on Mar. 26, 2018, which claims the benefit of U.S. Provisional Patent Application No. 62/478,828, filed on Mar. 30, 2017. These applications are hereby incorporated by reference herein.

BACKGROUND

Vector flow imaging (VFI) can be used to visualize and quantify complex blood flow measurements in cardiovascular applications for better diagnosis of stenosis and other conditions of the vascular system. Since conventional Doppler ultrasound only allows velocity estimation along the axial direction, new vector flow imaging techniques have been introduced to allow multi-directional velocity estimations. These new techniques include fixed-arrow-based (see FIG. 7A, free-arrow-based (see FIG. 7B), and pathlet-based visualization (see FIG. 7C).

For fixed-arrow-based visualization, the magnitude of flow velocity is encoded as color intensity, and is proportional to the length of the arrow. The direction of flow velocity is shown both by the arrow and color. The tail of the arrow is fixed in space. For free-arrow-based visualization, free arrow is used to dynamically track the blood flow. The magnitude of flow velocity is color encoded, and is proportional to the length of the arrow. The direction of flow velocity is indicated by the arrow. In the context of VFI, streamline may be defined as a family of curves that are instantaneously tangent to the velocity vector of the flow, and a pathline can be defined as a family of trajectories that the flow particles would faithfully follow during flow.

For pathlets-based visualization, dynamic curve tracing of the flow trajectory is achieved by curved pathlets. Pathlets can be seen as the short, frontal segments or parts of the pathlines, that start to fade out when distance from the tip exceeds a given threshold, which is defined as the pathlet length. The magnitude of flow velocity is color encoded, and is proportional to the length of the pathlets. The direction of flow velocity is indicated by the moving direction of pathlets. Overall, among the three visualization methods, pathlet-based visualization is generally the most intuitive method with potential to replace the other visualization methods for VFI.

While an improvement over Doppler, existing implementations of these VFI techniques may still have limitations. For example, in existing fixed-arrow-based visualization specifically, the color-coding map for velocity magnitude and direction is complex and not intuitive. Additionally, the length of the arrow is not a direct measurement of velocity magnitude. In existing free-arrow-based visualization techniques, the arrows are typically straight lines and may not be good representations of curved trajectories and having an arrowhead for each streamline may clutter the visualization and thus be less intuitive. Also, in existing free-arrow-based and pathlets-based visualizations, neither the coded color map nor the length of the arrow (pathlet) is a direct measurement of velocity magnitude. Consequently, direct measurements and accurate quantification of blood flow are unavailable. Additional shortcomings of existing VFI techniques may include the inability to perform point measurements of blood flow at certain locations of interest, which can further limits the capability of VFI to extract detailed spatiotemporal information of blood flow. Examples in accordance with the present disclosure may address one or more of the shortcomings of existing VFI systems and methods.

SUMMARY

The present invention provides systems and methods for concurrent ultrasound vector flow imaging (VFI) with automatic curve tracking. The examples described herein may overcome limitations of existing VFI techniques, for example by providing more user friendly and/or interactive displays of VFI image data to enable the user to select specific points within the blood flow, obtain the velocity magnitude at a selected point, and/or by utilizing arrow displays to more intuitively visualize the velocity vector data at the user selected points.

A system for visualization and quantification of ultrasound imaging data in accordance with the present disclosure may include a display unit, and a processor communicatively coupled to the display unit and to an ultrasound imaging apparatus for generating an image from ultrasound data representative of a bodily structure and fluid flowing within the bodily structure. The processor may be configured to generate vector field data corresponding to the fluid flow, wherein the vector field data comprises axial and lateral velocity components of the fluid, extract spatiotemporal information from the vector field data at one or more user-selected points within the image, and cause the display unit to concurrently display the spatiotemporal information at the one or more user-selected points with the image including a graphical representation of the vector field data overlaid on the image, wherein the spatiotemporal information includes at least one of a magnitude and an angle of the fluid flow. In some embodiments, the ultrasound imaging apparatus may be provided by an ultrasound diagnostic system including the display and the processor, and the ultrasound diagnostic system may be configured to generate and update the image in real-time while ultrasonically imaging the bodily structure.

In some embodiments, the processor may be configured to generate a pathlet-based graphical representation of the vector field data. In some embodiments, the graphical representation of the vector field data may include a vector map that includes a flow mask layer defining a sub-region corresponding to the vector field data and a vector visualization layer illustrating at least partial trajectories of velocity vectors in the sub-region. In some embodiments, the processor may be configured to define the flow mask based on image segmentation, available vector field data (e.g., blood flow velocity data), user input, or combinations thereof.

In some embodiments, the processor may be configured to dynamically update the flow mask in subsequent image frames based on temporal variations of available velocity estimates in subsequent vector flow frames. In some embodiments, the processor may be configured to generate the B-mode image and the graphical representation of a vector field in real time while acquiring the echo signals. In some embodiments, the processor may be configured to dynamically update the flow mask in subsequent image frames based on temporal variations of the available vector field data in corresponding vector flow frames. In some embodiments, the processor may be configured to cause the display unit to display, as the spatiotemporal information, a graph of the at least one of the magnitude and the angle of the fluid flow at the one or more user-selected points as a function of time. In further embodiments, the processor may be configured to cause the display unit to display, as the spatiotemporal information, a visual representation of a direction of the fluid flow at the one or more user-selected points, and the visual representation may be dynamically updated by the processor to reflect temporal changes in the direction of the fluid flow. In some embodiments, the visual representation of the direction of the fluid flow may be in the form of a graph of the axial component of the velocity vector versus the lateral component of the velocity vector at the one or more user-selected points. In further embodiments, the user-selected points may define a selected region including a plurality of adjacent points (e.g., a cluster of pixels on the displayed image) and spatiotemporal data may be displayed for each of the points in the selected region individually or in combination (e.g., as an average over the selected region).

In some embodiments, the vector flow data may also include elevational velocity components of the fluid, and the processor may be configured to generate a three dimensional (3D) image of the ultrasound data overlaid with a graphical representation of a 3D velocity vector field. In some embodiments, the processor may be configured to estimate the axial, lateral, and/or elevational velocity components of the fluid flow. For example, the system for visualization and quantification according to the present disclosure may be integrated with an ultrasound imagining system configured to acquire the ultrasound imaging data. In other embodiments, one or more of the components of the system may be part of a stand-alone visualization system communicatively coupled to a source of ultrasonic imaging data, which may be pre-stored or received in real-time. For example, at least one of the display and the processor may be part of a workstation separate from the ultrasound imagine apparatus, and may be configured to generate the ultrasound image from real-time or pre-stored ultrasound imagining data. In further examples, the processor may receive the estimated components as input and generate the image and extract spatiotemporal information for concurrent display with the image.

A method according to some embodiments of the present disclosure may include generating an image from ultrasound data representative of a bodily structure and fluid flowing within the bodily structure, generating vector field data corresponding to the fluid flow, wherein the vector field data comprises axial and lateral velocity components of the fluid, displaying, on a user interface, a graphical representation of the vector field data overlaid on the image, extracting spatiotemporal information from the vector field data at one or more user-selected points within the image, and concurrently displaying the spatiotemporal information at the one or more user-selected points with the image including the graphical representation of the vector field data, wherein the spatiotemporal information includes at least one of a magnitude and an angle of the fluid flow. In some embodiments, the method may include receiving, in a processor, signals responsive to ultrasonically scanning a region of interest (ROI) of a subject, and generating a B-mode image of the ROI responsive to the signals and estimating axial and lateral components of blood flow velocity within a sub-region of the ROI to obtain a vector field of the blood flow in the sub-region. Graphical representations of the vector field may be generated by the processor and concurrent displays of the vector field and spatiotemporal information about the vector field may be provided in accordance with any of the examples herein. In some embodiments, the graphical representation may be a pathlet-based graphical representation of the vector field.

In embodiments, the displaying of spatiotemporal information may include displaying a graph of the at least one of the magnitude and the angle of the fluid flow at the one or more user-selected points as a function of time. In some embodiments, the displaying of spatiotemporal information may include displaying a visual representation of a direction of the fluid flow at the one or more user-selected points, and the visual representation may be dynamically updated to reflect temporal changes in the direction of the fluid flow. In further embodiments, the visual representation of the direction of the fluid flow may be in the form of a graph of the axial component of the velocity vector versus the lateral component of the velocity vector at the one or more user-selected points. In yet further embodiments, the displaying of spatiotemporal information may include displaying information for the magnitude and the angle of the fluid flow, and wherein the displayed information and for the magnitude and the angle of the fluid flow are synchronously updated in real-time responsive to the signals received from a region of interest (ROI) in a subject. As described herein, one or more points may be selected by a user and spatiotemporal information may be provided for the selected points. In some examples, the selected points may include a plurality of adjacent points in the image (e.g., a cluster of points or a selected region) and spatiotemporal information may be displayed for each point in the selected region either individually or collectively (e.g., as an average) for all points in the elected region. In embodiments of the present disclosure, the displayed spatiotemporal information and the graphical representation of the vector field may be synchronously updated in real-time responsive to real-time signals received from the ROI. In some embodiments, the graphical representation of the vector field data may include a vector map comprising a flow mask layer delineating a region corresponding to the vector field data in that frame and a vector visualization layer illustrating at least partial trajectories of at least some of the velocity vectors in the vector field data in that frame In some embodiments, the method may further include estimating elevational velocity components of the fluid to obtain three dimensional (3D) vector field data for a volumetric region of interest (ROI). In such embodiments, the concurrent displaying of spatiotemporal information at the one or more user-selected points with the image may include displaying 3D image of the volumetric ROI overlaid with the 3D vector field data.

Any of the methods in accordance with the present disclosure, or steps thereof, may be embodied in non-transitory computer-readable medium comprising executable instructions, which when executed may cause a processor of medical imaging system to perform method or steps embodied therein.

DESCRIPTION

Figure 1:
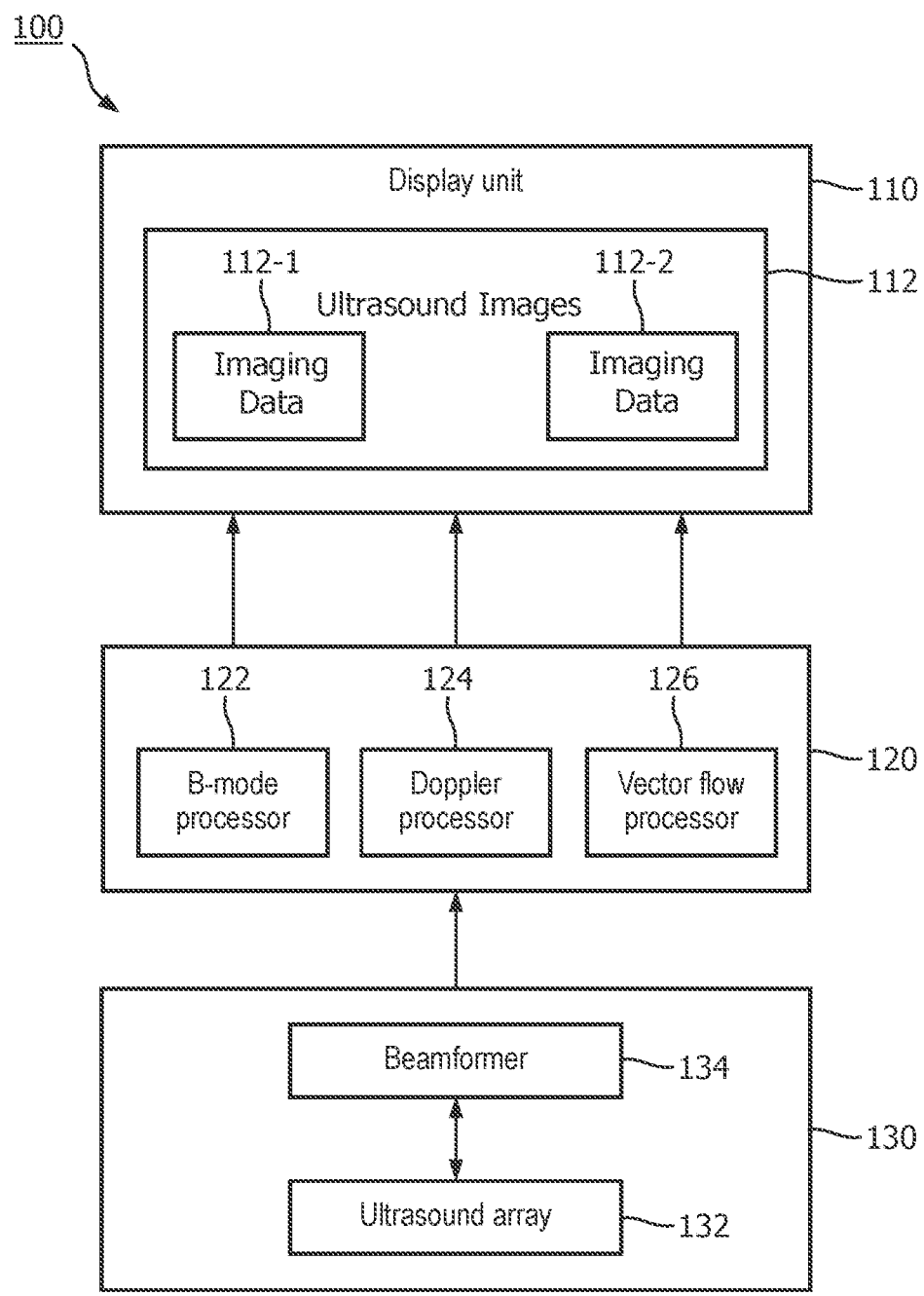
FIG. 1 is block diagram of a visualization and quantification system in accordance with the present disclosure.

The following description of certain exemplary embodiments is merely exemplary in nature and is in no way intended to limit the invention or its applications or uses. In the following detailed description of embodiments of the present systems and methods, reference is made to the accompanying drawings which form a part hereof, and in which are shown by way of illustration specific embodiments in which the described systems and methods may be practiced. These embodiments are described in sufficient detail to enable those skilled in the art to practice the presently disclosed systems and methods, and it is to be understood that other embodiments may be utilized and that structural and logical changes may be made without departing from the spirit and scope of the present system. Moreover, for the purpose of clarity, detailed descriptions of certain features will not be discussed when they would be apparent to those with skill in the art so as not to obscure the description of the present system. The following detailed description is therefore not to be taken in a limiting sense, and the scope of the present system is defined only by the appended claims.

Conventional techniques for visualizing blood flow rely on the Doppler estimation method, which can only provide velocity estimation along the axial direction. In Doppler imaging, a binary output of the direction of blood flow (i.e., towards or away from the ultrasound beam) and the magnitude of the velocity in this direction is estimated, which may not provide sufficient information to a clinician, particularly in applications where understanding the complex blood flow is critical. Vector flow imaging techniques have emerged to address some of the shortcomings of conventional Doppler. Vector flow imaging (VFI) provides angle-independent multi-directional velocity estimation of blood flow velocity.

In accordance with examples herein, a system configured for VFI may include, alternative to or in addition to a conventional Doppler processor, a vector flow processor which performs flow estimation over a region of interest (ROI) to independently obtain the axial and transverse velocity components of the velocity vector at any given location within the ROI. From the axial and transverse velocity estimates, a magnitude and angle of the velocity at any given point or pixel in the ROI can be obtained and visualized. Vector flow estimation may be performed in accordance with any known techniques, for example using a transverse oscillation approach, synthetic aperture imaging, or ultrafast or continuous imaging, e.g., as described in publications by Evans et al., in "Ultrasonic colour Doppler imaging," Interface Focus, vol. 1, no. 4, pp. 490-502, August 2011, and by Jensen et al., in "Recent advances in blood flow vector velocity imaging," 2011 IEEE International Ultrasonics Symposium, 2011, pp. 262-271, the contents of which publications are incorporated herein by reference in their entirety for any purpose. It has been recognized that in providing real-time vector flow data, VFI presents new challenges due to the wealth of information now obtainable through this new imaging technique. For example, in the case of turbulent flow, for example around bifurcations or valves where such rapid changes are often observed, the flow velocity and direction may change rapidly, which can make it difficult to perceive all clinically relevant details by simply visualizing the vector flow field. To perceive clinically relevant changes in the blood flow, a clinician may need to observe a slow moving cine-loop or study still frames of the vector field, which can be time consuming and cumbersome. New solutions for enhancing the visualizing and quantification of vector flow data may be obtained via the systems and methods described herein, which can improve the clinical utility of VFI imaging.

FIG. 1 shows a system for visualization and quantification of ultrasound imaging data in accordance with some examples of the present disclosure. The system includes a display unit 110 and a processor 120. The processor 120 may be communicatively coupled to an ultrasound imaging apparatus 130 to receive ultrasound imaging data, for example ultrasound imagining data received in real time while a subject is ultrasonically scanned. The ultrasound imaging apparatus 130, also referred to herein as ultrasound scanner, may include an ultrasound array 132 that may be housed in an external or an intravascular probe, and a beamformer 134, which may operate under the control of an imaging controller to direct ultrasound beams and receive ultrasound echoes from a subject (e.g., a patient) using the ultrasound array 132, which are then beam-formed and transmitted to one or more processors for further processing and image generation. In some embodiments, the processor 120 and/or the display unit 110, or components thereof (such as one or more of the processors 122, 124, and 126), may be integrated with the ultrasound imaging apparatus 130, which may for example be any of the ultrasound imaging system, such as the SPRAQ or the EPIQ ultrasound system, provided by PHILIPS. In some examples, the processor 120 may additionally or alternatively be configured to receive ultrasound imaging data, for example imaging data from an imaging session performed prior to visualization and quantification of the data by a clinician, and which has been stored in memory (e.g., memory storage device of a picture archiving and communication system (PACS)) for later access by the processor 120.

The processor 120 may be configured to generate ultrasound images 112 for display on the display unit 110. To that end, the processor may include a B-mode processor 122 configured to generate B-mode images and a Doppler processor 124 configured to generate Doppler images (e.g., color-flow Doppler, spectral Doppler, and power Doppler such as Color Power Angio (CPA) images). In some examples, images may be displayed as overlays of imaging data obtained from multiple imaging modes. For example in duplex (e.g., B-mode/Doppler) imaging, a gray-scale image of the anatomy (i.e., a B-mode image) may be overplayed with color-flow Doppler data to provide, for example, a color-flow Doppler image. In accordance with the present disclosure, the processor 120 may include a vector flow processor 126 configured to generate vector flow imaging data based on the ultrasound imaging data (e.g., real-time or pre-stored imaging data), which data may be overlaid on background D-mode images similar to B-mode/Doppler duplex imaging. In some embodiments, the system may include only a vector flow processor, while the B-mode image data and/or images and Doppler image data and/or images are generated by an ultrasound scanner and stored in memory (e.g., PACS), for access and overlay with the vector flow imaging data generated by the visualization system. In other embodiments, B-mode, Doppler, and vector flow imaging data is generated in real time and visualization and quantification may be performed in real time (i.e., during the acquisition of the ultrasound imaging data). In some embodiments, the functionality of one or more of the processors (e.g., B-mode processor 122, Doppler processor 124, and vector flow processor 126) of system 100 may be integrated into a single or a fewer number of processors such as a specially programmed CPU or GPU operable to perform the functions of these processor described herein.

Information extracted from the vector flow imaging data may be rendered on the display unit 110 in the form of vector flow visualization data (e.g., a 2D or a 3D vector map) and/or spatiotemporal visualization data. The vector flow visualization data provides a graphical representation of the vector field, which may be in the form of a 2D or a 3D vector map. The spatiotemporal visualization data provides a graphical representation of quantitative information about one or more velocity vectors visualized as a function of time. For example, spatiotemporal visualization data may be graphically represented using various plots or graphs, such as graphs of the magnitude or angle of a velocity vector any given point (e.g., a user-selected point) as a function of time, or as dynamically updated graph displaying the direction of a single or a plurality of velocity vectors isolated from the larger vector field, e.g., responsive to user input. In some examples, the quantification may be performed for a small selected region which may include a plurality of points or pixels. In such examples, the spatiotemporal visualization data may include a plurality of traces (i.e., a trace for each of the set of points or pixels in the selected region), and the plurality of traces may be presented in a single graph or in separate graphs. In yet further embodiments, the spatiotemporal information may be averaged over the plurality of points of the selected region and a single graph of the averaged values may be provided on the display. The vector flow visualization data and spatiotemporal visualization data may be displayed concurrently (e.g., side-by-side, or as an overlay) with imaging data from other modes, for example as an overlay or a side-by-side display with B-mode image data. Thus, in accordance with the examples herein, the processor 120 is configured to cause the display unit 110 to concurrently display at least two types of imaging data 112-1 and 112-2, as will be further described.

Vector flow imaging data generated by the vector flow processor 126 may be visualized using any suitable visualization technique, such as fixed-arrow based, free-arrow based, and pathlet-based visualization. For fixed-arrow-based visualization, the magnitude of flow velocity is typically encoded as color intensity, and is proportional to the length of the arrow. The direction of flow velocity is typically shown both by the arrow and color. The tail of the arrow is fixed in space. For free-arrow-based visualization, free arrows are used to dynamically track the blood flow. The magnitude of flow velocity is typically color encoded, and is proportional to the length of the arrow. The direction of flow velocity is indicated by the arrow.

In the context of VFI, a streamline may be defined as a family of curves that are instantaneously tangent to the velocity vector of the flow, and a pathline can be defined as a family of trajectories that the flow particles would faithfully follow during flow. For pathlets-based visualization, dynamic curve tracing of the flow trajectory is achieved by curved pathlets. Pathlets can be seen as the short, frontal segments or parts of the pathlines, that start to fade out when distance from the tip exceeds a given threshold, which is defined as the pathlet length. The magnitude of flow velocity is color encoded, and is proportional to the length of the pathlets. The direction of flow velocity is indicated by the moving direction of pathlets. Overall, among the three visualization methods, pathlet-based visualization may be deemed the most intuitive method with potential to replace the other visualization methods for VFI.

Figure 2:
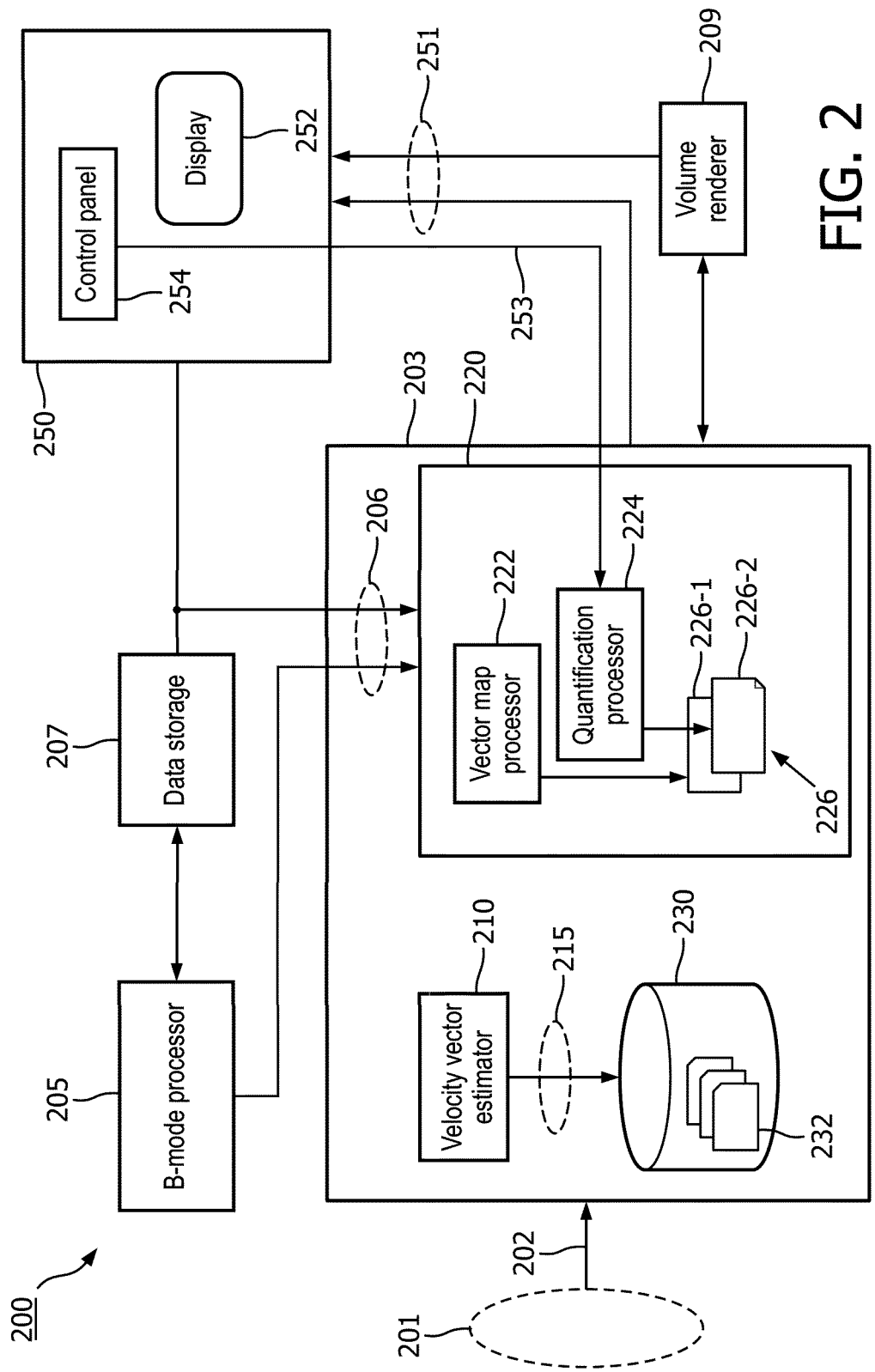
FIG. 2 is a block diagram of a visualization and quantification system in accordance with further examples of the present disclosure.

FIG. 2 shows an example of a system 200 for visualization and quantification of vector flow data. The system 200 in FIG. 2 may utilize pathlet-based visualization or any other suitable technique to visualize the vector field. The system 200 may include a vector flow processor 203, which is coupled to a source of ultrasound imaging data. For example, the ultrasound imaging data 202 may be received (e.g., in real time) from an ultrasound imaging apparatus (e.g., ultrasound scanner) responsive to ultrasonically scanning a region of interest 201. In some examples, the vector flow processor 203 may be communicatively coupled to a B-mode processor 205. The B-mode processor may also be coupled to the source of ultrasound imaging data to generate background grayscale images for display with the vector flow data. The vector flow processor 203 may additionally or alternatively be coupled to a data storage device 207 (e.g., memory of an ultrasound imaging apparatus or PACS), which may store ultrasound imaging data and/or B-mode images.

In accordance with the examples herein, the vector flow processor 203 may be configured to generate a graphical representation of a vector field representative of blood flow in a region of interest (ROI). For example, the vector flow processor 203 may include a velocity vector estimator 210, a visualization processor 220, and a frame buffer 230 (also referred to as VFI memory 230). The frame buffer 230 may store frames of data used at various stages of the VFI process. For example, the frame buffer 230 may store frames of vector field data generated by the velocity vector estimator 210. The frame buffer 230 may store frames of visualization data before it is overlaid on background images and/or combined with other graphical information (e.g., annotations) for display. As described herein, velocity vector estimation may be performed by the velocity vector estimator 210 in accordance with any suitable technique, several of which have been developed and can be used herein, to obtain a velocity vector field for the ROI. In some examples, ultrafast Doppler imaging (e.g., using plane wave imaging) may be performed at sufficiently high pulse repetition frequency (PRF) in order to obtain sufficiently high frame rates to enable velocity vector estimation. At the end of the vector estimation process, which is outside of the scope of this disclosure as it may be implemented using known vector extraction techniques, a vector field 215 for each image frame may be generated and passed to the frame buffer 230. The vector field frame data 232 may be stored in the buffer 230 until it is accessed by the visualization processor 220 for generating vector flow images 226.

In accordance with the examples herein, the vector flow processor 203 may be configured to cause a display unit of the system (252) to display an ultrasound image of the graphical representation of the vector field (e.g., vector map) overlaid on a B-mode image of the ROI. The vector flow processor 203 may receive an indication of a selected region within the vector field, for example responsive to user input 253 received via the control panel 254 of user interface 250. The vector flow processor 203 may be configured to then update the ultrasound image to display spatiotemporal information about the vector field at the selected region. For example, the visualization processor 220 may include a vector map processor 222 configured to produce vector flow visualization data 226-1 (e.g., a vector map), and may further include a quantification processor 224 configured to generate spatiotemporal visualization data 226-2 (e.g., a graph of a vector quantity dynamically updated over time). In a similar manner to traditional duplex color-flow or power Doppler images, background B-mode images 206 (e.g., real-time or stored B-mode images) may be overlaid with the vector flow visualization data 226-1 (e.g., the vector map) and displayed in a duplex B-mode/VFI mode. Spatiotemporal visualization data 226-2 may be provided concurrently with the display of the duplex B-mode/VFI mode image.

As will be further described, spatiotemporal information may be provided at one or more selected points in the vector field. Points for quantification may be selected by the user. For example, a selected region that includes a single point may be selected by a single click at any desired location within the displayed vector field. Upon the selection of a region that includes a single point for quantification, a single trace would be provided on the display that corresponds to selected point. Additional points may be subsequently selected by the user in the same manner, e.g., by clicking on any other point within the displayed vector field, responsive to which additional traces corresponding to the additional selected points would be added to the spatiotemporal display. A selected region that includes a plurality of points may be selected by the user by placing the cursor at any desired location within the displayed vector field and dragging the cursor to define the desired grouping of pixels to be included in the selected region. Upon selection of a region of multiple points, either a single trace averaging the velocity information over the region would be displayed or a plurality of traces, one for each point in the selected region, may be provided in the spatiotemporal display.

Alternatively or additionally, points may be automatically selected by the system (e.g., by the vector flow processor 203), such as based on a pre-set default for a given clinical application or based on assessment of the vector flow data. For example, in the case of the latter, the vector flow processor 203 may sample a set of consecutive frames of vector flow data to identify one or more locations in the vector field exhibiting turbulence and select a point at the location of maximum turbulence. In other examples, such as when imaging a relatively laminar flow through a vessel, the system may default the selected point at a location along the centerline of the vessel, which may be identified using image processing techniques (e.g., segmentation). In other embodiments, image processing techniques may be used to identify clinically relevant landmarks of the ROI being imaged and locate the selected point(s) at one or more of the clinically relevant landmarks. The default selected point may be used to initially provide spatiotemporal information until the user moves/removes the default point and/or selects another point. In some embodiments, spatiotemporal information may be displayed only after the user has selected a point in the vector field (e.g., after the visualization of the vector field has been provided to the user). In such embodiments, the ultrasound image displaying the vector flow visualization data may be updated once the user selects a point, to provide the spatiotemporal information concurrently with the continued display of the vector flow visualization data, both of which may be updated in real time. In some embodiments in which spatiotemporal information is not initially provided, place holder graphical elements (e.g., a blank graph window displaying the axes or other information, such as labels, about the information be provided) may be provided on the display, and the place holder graphical elements may only being to update with spatiotemporal information after the user has selected the desired point for quantification.

In further embodiments, the spatiotemporal information may be an amount of blood flow or quasi- (i.e., 2D) or volumetric flow rate through the vessel, which may be estimated from the vector flow data. For example, the system may receive an indication of a location along the length of the vessel and define a flow boundary (e.g., a line in the case of 2D or area in the case of 3D visualization). In other embodiments, the system may automatically define the boundary at a location generally centered along the length of the vessel or at a location of highest turbulence within the imaged ROI. The boundary may be defined so that it is generally perpendicular to the lumen at the selected location or it may be generally aligned with the axial direction. The system may then estimate the amount of flow that passes through the boundary and plot this estimate as a function of time. In some embodiments, the system may provide a spatiotemporal display of vector flow information across a boundary, for example by plotting the values of the magnitude of the velocity at each point along the boundary (this information can be plotted on the y axis), as a function of time. Additionally, this spatiotemporal display may be color-coded to also provide the angle of the flow at each spatial location across the boundary. Other spatiotemporal displays may also be provided to visualize the flux across or along the vessel which may aid in diagnosis of vascular disease (e.g., plaque severity and/or risk of plaque rupture).

Figure 3:
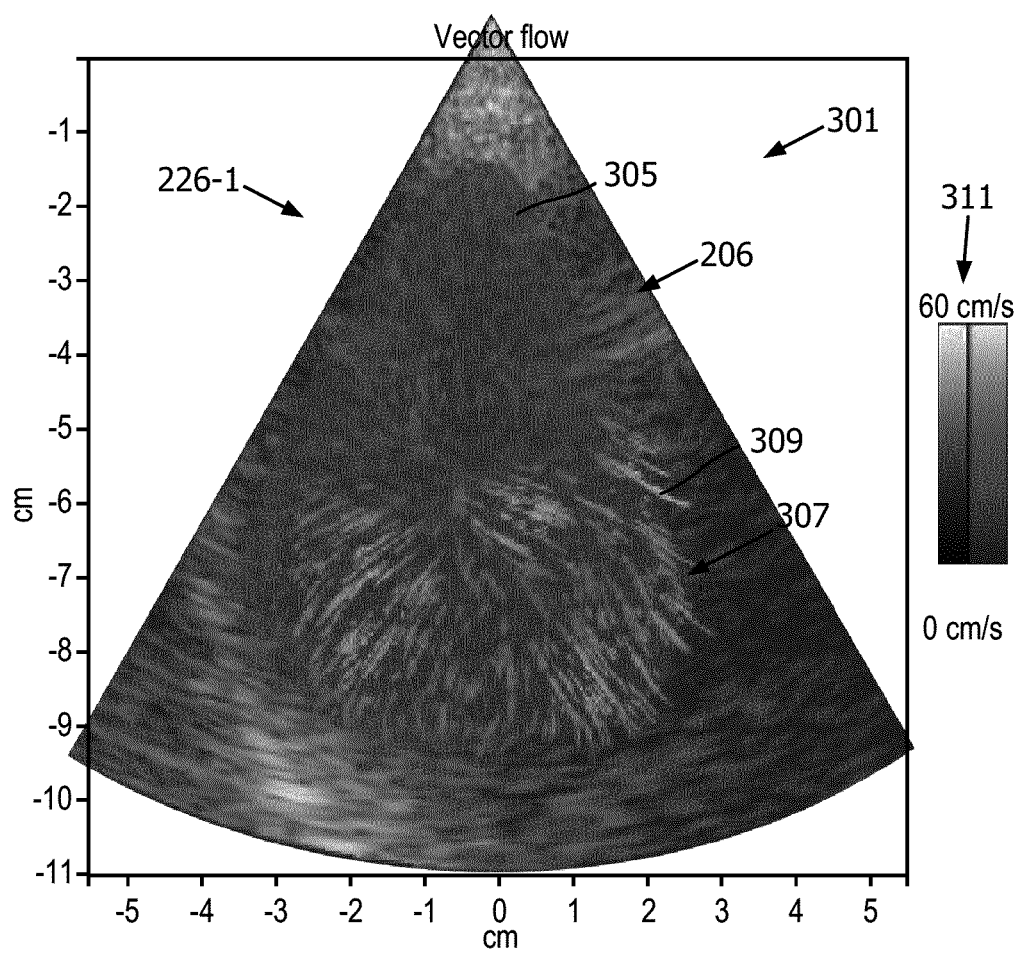
FIG. 3 is an ultrasound image generated in accordance with examples of the present disclosure, which includes a background B-mode image overlaid with a vector flow image visualizing the blood flow pattern within the left ventricle of a human heart.
Figure 4:
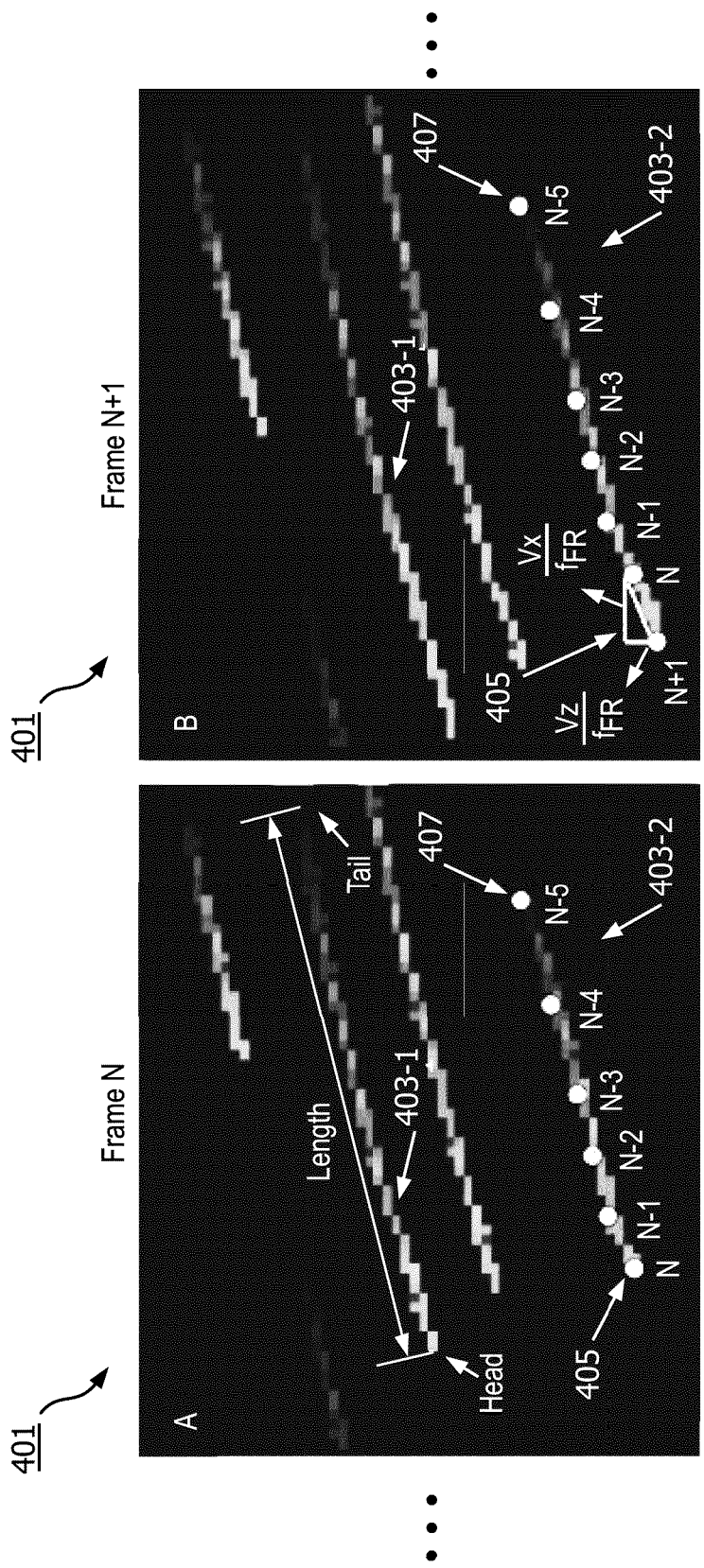
FIG. 4 shows an illustration of a portion of two consecutive frames of ultrasound image data and a technique for updating the pathlet-based information in the frames.
Figure 5:
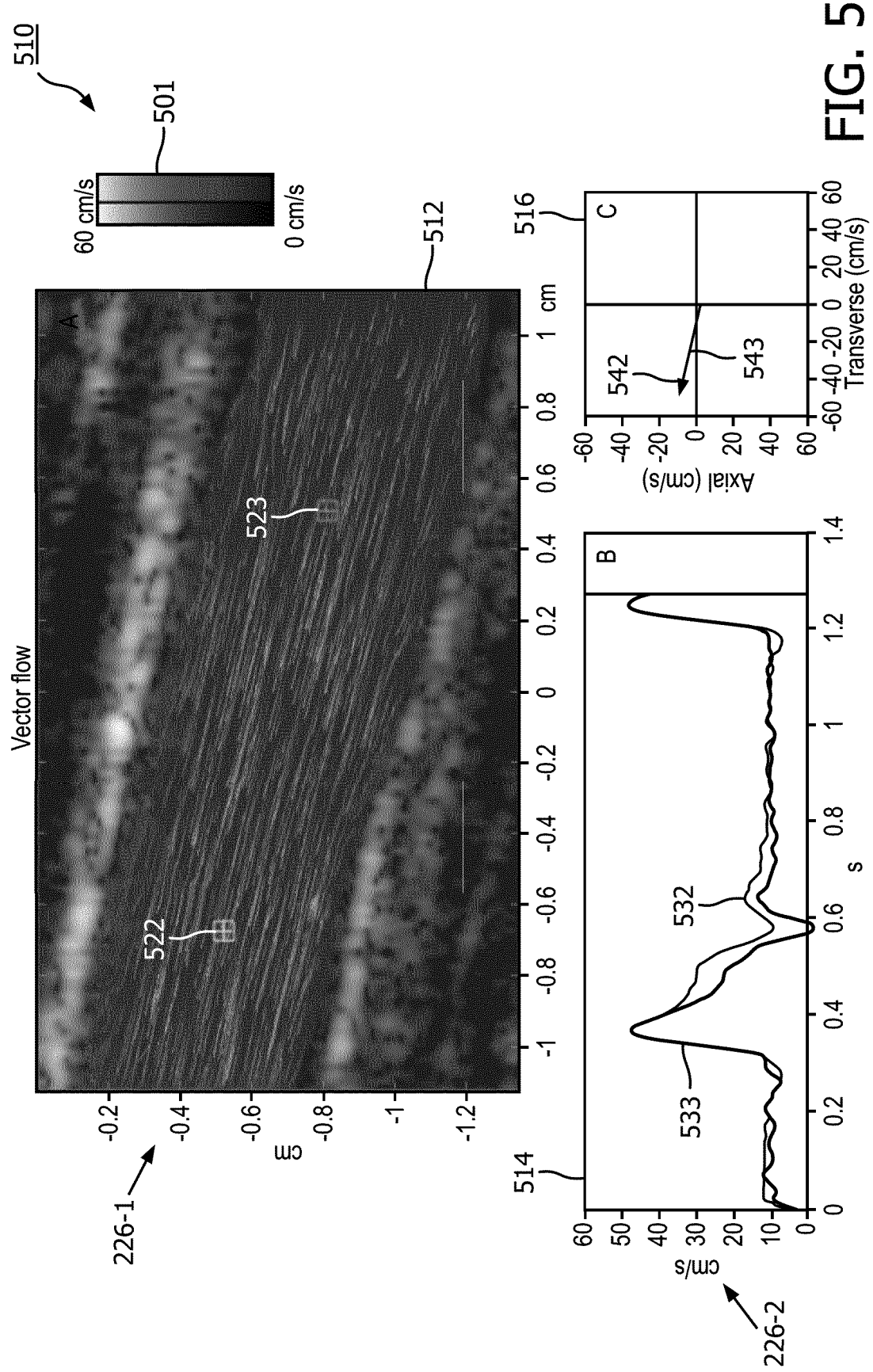
FIG. 5 shows a screen capture of a display unit displaying an example set of images generated in accordance with the present disclosure, which display a relatively smooth blood flow in a vessel.

In some embodiments, the processor (e.g., vector flow processor 203) of the visualization and quantification system (e.g., system 200) may be configured to generate a pathlet-based representation of the vector field. FIGS. 3-5 illustrate examples of pathlet-based graphical representations of a vector field in accordance with some examples. While an example VFI technique using a pathlet-based visualization is described with reference to FIGS. 3-5, it will be understood that the visualization and quantification systems and methods described herein are not limited to implementations using pathlet-based visualization and can similarly be utilized with other vector flow imaging visualization techniques. Other VFI techniques, including but not limited to fixed-arrow based or free-arrow based techniques, may also be used.

The vector flow visualization data 226-1 in the case of pathlet-based visualization may be provided in the form of a vector map 301, which include two components, as illustrated in FIG. 3: 1) a flow mask layer 305 delineating the flow region in a primary color (e.g., dark red or another) with a desired baseline transparency, for example 50%, so as to not completely obfuscate the background image (B-mode image 206), and 2) a vector field layer 307 illustrating the trajectories 309 of flow particles, which in this example are shown using pathlets.

In some embodiments, the flow region for which vector flow estimates are obtained and thus vector flow visualization performed may be user-defined, such as responsive to a user selection of a sub-region within the imaged ROI. In such embodiments, the size and shape of the flow mask layer 305 and correspondingly the vector field layer 307 are user-defined. This region selected by the user for vector flow visualization is not to be confused with the subsequently selected region for quantification, which may include a single or a subset of points within the vector flow visualization region. In other embodiments, the flow region for which vector flow visualization is performed may be automatically defined by the system, e.g., example using image segmentation or other suitable image processing techniques such as to identify the walls of the vessel. In such embodiments, the system (e.g., vector flow processor 203) may define the flow region to include the area inside an imaged vessel, and correspondingly a flow mask layer 305 and vector field layer 307 are produced for all points/pixels within the system-defined flow region.

In yet further embodiments, the flow region for which vector flow visualization is performed may be automatically defined by the system (e.g., vector flow processor 203) based on available blood flow velocity data (i.e., based on points/pixels in the image which are associated with detected blood flow in any given frame). In such embodiments, the system may generate a flow mask layer 305 and corresponding vector field layer 307 for the system-defined flow region by including within the flow region all points/pixies in the image for which velocity estimates are available in any given frame. In such embodiments, the system (e.g., vector flow processor 203) may automatically update the vector flow image to reflect temporal variations in the blood flow velocity data. That is, as blood flow varies from frame to frame (e.g., responsive to the different phases of the cardiac cycle), the flow mask layer 305 corresponding vector field layer 307 may be dynamically updated from frame to frame to reflect this variation. Thus, the displayed vector field map may have a different shape or size in different frames (see e.g., FIGS. 6A and 6B). A combination of any of these or other suitable techniques may be used to define the flow region.

As described, pathlets for visualizing the vector field may be generated and updated in real-time (e.g., a frame of vector flow visualization data may be generated for each frame of image data) and overlaid on the flow mask to produce a vector flow image, which is then overlaid onto the corresponding B-mode image frame for display (e.g., on display unit 252). In this manner, e.g., by updating the pathlets in real time, the vector flow image may provide a visual cue of the movement of the tracked particles (e.g., blood flow). Each pathlet begins fading out when a distance from the tip exceeds a given threshold. That is, a head of the pathlet is always more opaque than the tail, enabling easier identification of the moving direction (i.e., flow direction) of the pathlet, even in a static image, without the inclusion of arrows that may clutter the display. Additionally, the pathlets may be color-coded and/or the pathlet length may be proportional to the velocity magnitude, both of these features helping the user more easily visualize the velocity magnitudes.

FIG. 4 shows partial magnified images of two consecutive frames 401 (i.e., frames N and N+1) of a pathlet-based vector map, which includes pathlets 403-1 and 403-2. The pathlets in the vector map, as well as the vector map generally, may be defined using several parameters, including length (alternativley, or additional and optionally, duration), width, and density of pathlets, generation rate of new pathlets (or alternatively vanish rate of old pathlets), color range for mapping of pathlets, display frame rate, and transparency and color of the flow mask, any of which parameters may be user-configurable (before or during imaging) to obtain a desired visualization effect without compromising the diagnostic performance of the system.

To generate the pathlets, initially a number of frames of the vector field data are saved and pathelts are generated for each frame, for example by interpolating the trajectory of tracked particles over the number of initial frames. For each subsequent frame, the pathelts are updated based on the velocity vector data associated with the subsequent frames. For example, in FIGS. 4A and 4B, the pathlets 403-1 and 403-2 illustrate the frontal portion of the trajectories of two tracked flow particles, the last several locations of one of which are shown by the points N+1, N, N−1, N−2, N−3, N−4, and N−5 which for illustration are so labeled to indicate the frame with which they are associated. The front most point in each frame indicates the estimated location of the tracked particle in that frame. The front most point of the pathlet in each frame (e.g., point N in frame N and point N+1 in frame N+1) is referred to as the head 405 of the pathlet. The pathlets may be updated every frame to reflect the movement of the particle to a new location and thus this movement may be visualized on the display by the changing location of the head 405 of the pathlet in each updated frame. The new location of the tracked particle and thus the head 405 is calculated using the angle-independent velocity estimates (i.e., the axial and lateral velocity components in the case of a 2D map or the axial, lateral and elevational velocity components in the case of a 3D map), which can be obtained in real-time or prior to the visualization. For example the axial displacement of the tracked particle may be calculated as Vz/fFR and the lateral displacement of the tracked particle may be calculated as Vx/fFR, where Vx is the lateral velocity (m/s), Vz is the axial velocity (m/s) of the head, and fFR is the tracking frame rate (Hz). A continuous and smooth pathlet is generated by interpolation (linear or cubic) of these discrete dots, and then displayed as an aliasing-free line.

Overtime, the aft end of a particle's trajectory fades, e.g., to reduce clutter on the display, and only the frontal portion of the trajectory is shown on the display. The aft end of the displayed pathlet is referred to as the tail 407 of the pathlet. The pathlets (e.g., pathlets 403-1 and 403-2) may be color-coded based on the velocity magnitude at different locations (i.e., each segment 409 between the location of the particle in a previous frame and the location of the particle in the he current frame may reflect the estimated velocity magnitude of the particle in the current frame). A color map key 311 (see FIG. 3) for the vector map may be displayed concurrently with the vector flow image. In addition to color-coding, the transparency of each pathlet may be linearly distributed with the highest opacity at the head 405 and decreasing to lowest opacity at the tail 407. The transparency distribution may also be updated at each frame. That is, when a new segment 409 is added in a new frame, the transparency may be linearly re-distributed with highest opacity (e.g., 50% or other) at the head 405 and decreasing to e.g., 100% transparency at the tail 407. The transparency may be linearly distributed, such as on a per pixel basis along the length of the pathlet or on a per segment basis. In this manner, the transparency distribution of the pathless may enhance the ease in identifying the direction of flow, even in a static image.

As previously described, each pathlet may have a maximum length, which may be pre-set or user defined. As the pathlet is update frame to frame, it grows in length in each frame due to the addition of a new segment at the head while maintaining the same tail. Once the pathlet reaches its maximum length (e.g., after being updated certain number of frames), it maintains a length shorter than the maximum length by deletion of the oldest location of the particle and correspondingly the aft most segment (also referred to as tail segment). If the pathlet is further defined by duration, with each frame in which the pathlet is updated, a lifetime variable of the pathlet is incremented until the lifetime variable of a given pathlet reaches the maximum lifetime, at which point the pathlet is removed from the display. For example, alternatively or additionally, each pathlet may have a lifetime, which can be defined using an integer variable randomly generated between the maximum pathlet length and the maximum lifetime when the pathlet is created. The age of a pathlet is decrease by one for each frame (e.g., every time the pathlet is updated). Once the age reaches zero, the pathlet is deleted from the vector map. A new pathlet may be created at the same time or in a different frame with another random lifetime assigned to it. With this lifetime feature, a balanced spatial distribution of pathlets may be maintained.

The pathlets may be updated using an iterative process for any subsequent frame. When the inputs (e.g., array variables including lateral position (x), axial position (z), lateral velocity $V_x$, and axial velocity ($V_z$), and two integer variables including "head of pathlet", and "lifetime of the pathlet") are received by the vector flow processor, the locations and lifetimes of the pathlets are examined. If a pathlet is located within the flow region, and its lifetime is greater than zero, it is defined as an active pathlet. If the pathlet moves outside of the flow region, or its lifetime is zero, it is defined as an inactive pathlet. For any active pathlets, the new head is computed based on the velocity maps, and the lifetime decreased by one. Any inactive pathlets are deleted from the display. An inactive pathlet may be replaced with a new pathlet for example, by randomly generating a new location and a new lifetime for the replacement pathlet. After the data structure for each pathlet is updated, the vector flow processor may generate (e.g., by interpolation) a smooth and continuous aliasing-free line to visualize the pathlets. The color of the line corresponding to each pathlet is coded based on the velocity magnitudes and the transparency of the color-coded pathlet is distributed along its length (i.e., from the new head to new tail of the pathlet) for rendering on the display.

Referring back to FIG. 2, the system may include a display unit 252, which may be part of a machine-user interface 250, which may include a user control unit 842 (e.g., a control panel). In some embodiments, the user control unit and display unit 252 are integrated in a touch-sensitive display which is operable to both display the images 251 and receive user inputs. Commands 253 responsive to the user inputs may be transmitted to the vector flow processor 203 for example for controlling the generation of spatiotemporal image data and/or other aspects of the display.

Referring now also to FIGS. 5 and 6, examples of ultrasound images generated for display by a visualization and quantification system of the present disclosure, for example system 200. The system may be configured to display an ultrasound image including at least two image components, one of which includes vector flow visualization data, the other including spatiotemporal data. In some examples, multiple spatiotemporal image components may be included in the ultrasound image to provide quantitative information about a plurality of different parameters or to visualize the same parameter in different ways.

FIG. 5 shows a screen capture 501 from a display unit (e.g. display 252) of a system built in accordance with the examples herein. The screen capture includes an ultrasound image 510 of a blood vessel. The image 510 includes a graphical representation of a vector field (in window A of the display) and spatiotemporal information associated with the vector field (in windows B and C of the display). The labels A, B, and C in the image in FIG. 5 are provided solely for ease of illustration and to facilitate understanding of the disclosure and may not be present in embodiments of the invention. Window A in FIG. 5 illustrated a first image element 512 that includes the graphical representation of the vector field, in this case a pathlet-based vector map 513. The vector map 513 may be generated and updated (e.g., in real time) in accordance with the examples herein (e.g., as described with reference to FIGS. 3 and 4. The vector map 513 is overlaid on a background B-mode image 515 of the imaged ROI. Windows B and C in FIG. 5 illustrate additional elements 514 and 516 of the image, specifically image elements that provide quantitative information about one or more points in the vector field visualized in Window A. Specifically, window B includes a graph of the magnitude of the velocity vector as a function of time for each of the selected points. In this illustrated example, two points have been selected (e.g., selected points 522 and 523) and two curves (temporal traces 532 and 533 corresponding to the points 522 and 523, respectively) are shown in window B. Each of the curves 532 and 533 traces the velocity magnitude (in cm/s, as shown on the y-axis) at each of the selected points as a function of time (in seconds, as shown on the x-axis). The blood flow through the vessel in this illustrated example is relatively laminar (i.e., without much variation in flow direction across the lumen) and exhibits relatively constant velocity magnitude over the displayed time sequence aside from expected variations in velocity magnitude due to the cardiac cycle (e.g., as evidence by an increase of flow velocity following systole around 0.4 seconds in the sequence). As will be further illustrated, more turbulent blood flow may be observed in other vessels, such as near the carotid bifurcation (see e.g., FIGS. 6A and 6B) and/or in the presence of plaque in a vessel. The visualization tools described herein may be particularly useful in extracting clinically useful quantitative information about the blood flow in such cases.

In use, a system for visualizing and quantifying blood flow according to the present disclosure may operate as follows. Once echo amplitude detection, e.g., for generating B-mode images, and velocity estimation, e.g., to generating vector flow information, have been performed, the system may render an ultrasound image, such as the image 510 in FIG. 5. This may occur in real-time (i.e., while imagining the subject) or after acquisition of the imaging data. In some embodiments, initially (e.g., prior to receiving user input selecting at least one point in the vector field), the image 510 may include only the image element 512. In other embodiments, placeholder elements 514 and 516, which may not provide any spatiotemporal information, may be included and only populated with the traces after the selection of the region (e.g., points) to be quantified. In yet further examples, both the vector flow and spatiotemporal information may be initially provided (e.g., in instances in which the system auto-selects a region for quantification).

In a subsequent step, the system may receive an indication of a selected region (e.g., a single point or a cluster of points selected responsive e.g., to a single click or a dragging of the pointer within the vector flow display in image 510). The vector flow display may be updating in real-time as the user makes the selection, or the user may freeze the display and make the selection in the frozen frame. Once a selection is made, the vector flow image (in window A) may automatically unfreeze, if previously frozen, and the system may add or begin to update the spatiotemporal elements of the image (e.g., elements 514 and 516 shown in windows B and C). The vector flow image as well as the spatiotemporal images may continue to update synchronously until the end of the temporal sequence, and in the case of real-time visualization, the updating occurs synchronously in all windows in real-time as data is being acquired by the system.

A variety of graphical elements may be used to provide the spatiotemporal displays. For example, the system may be configured to cause the displaying of a graph, which traces the changing velocity magnitude over time (e.g., as shown in window B). In other embodiments, instead of the magnitude, the angle of the velocity vector may be displayed as a function of time in window B or an additional graph may be provided to concurrently display the angle as a function of time. In some embodiments, the angle may be visually represented using a graph of the type shown in window C. In the graph in window C, the direction of flow at each of the selected points 522 and 523 are visualized by the respective arrows 542, 543, which are defined by the axial component of the velocity vector (y axis) versus the transverse or lateral component of the velocity vector (x axis). As with any other spatiotemporal image element, the graphs in window C is updated synchronously with the other elements of the image (e.g., windows A and B) to provide a dynamic visual representation of a single or a small number of blood flow velocity vectors that pass through the selected points.

In some examples, the system may be configured to receive as input a selection of a plurality of points, which may be received concurrently (e.g., as a selection of a small sub-region or cluster of points) or sequentially (e.g., one point selected after another), and the spatiotemporal displays may be updated responsive to any new selection made. For example, as shown in FIG. 5, the user may also select a second point 523 is selected by the user following the selection of point 522. Upon selection of an additional point, the system adds additional traces to the spatiotemporal displays to provide quantitative information about the additional selected points. Alternatively or additionally, the system may be configured to receive an indication of a selected region which includes a cluster of points or pixel (e.g., by dragging the cursor within the vector field to define the selected region), which case multiple traces for each point in the region may be concurrently displayed or a single averaging trace may be provided depending on the particular pre-set or user configuration of the system.

Figure 6A:
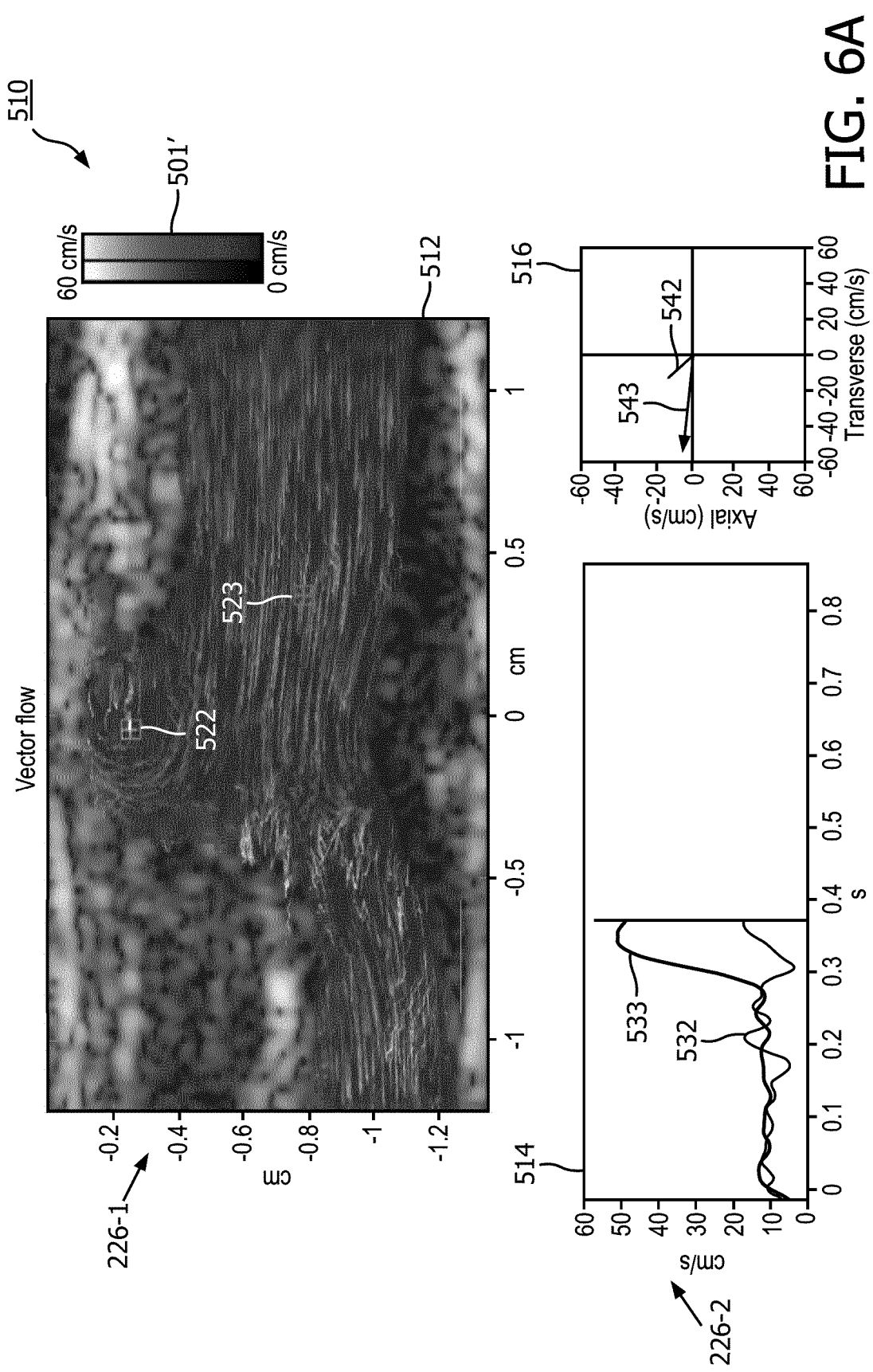
FIGS. 6A and 6B show other screen captures of a display unit displaying other example sets of images generated in accordance with the present disclosure, which show a more turbulent blood flow pattern within a human carotid artery.
Figure 6B:
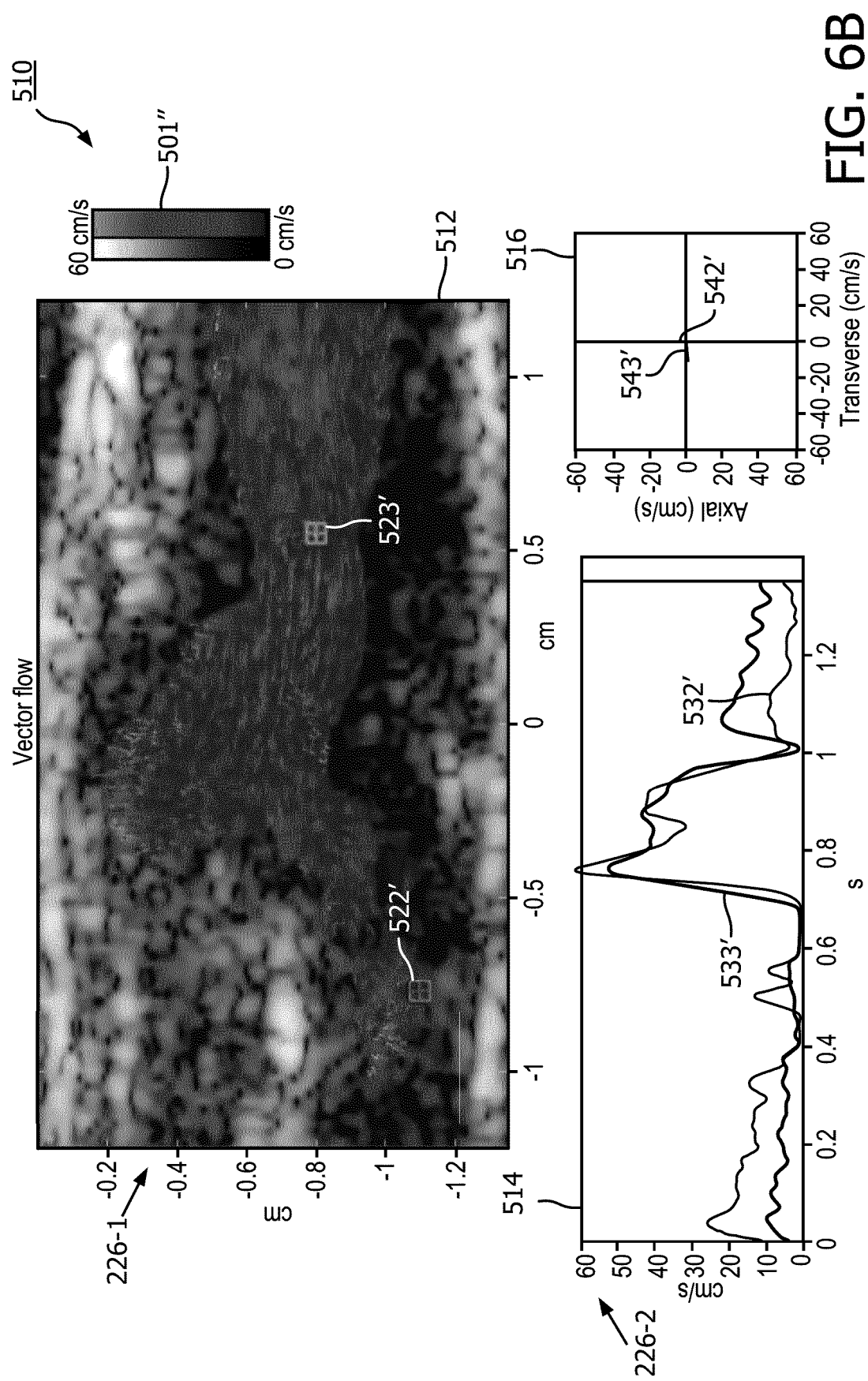

FIGS. 6A and 6B show additional screen captures 501' and 501" from a display unit (e.g. display 252) of a system built in accordance with the examples herein. These screen captures illustrate ultrasound images of the carotid artery and visualizations of the blood flow therethrough at various phases of the cardiac cycle. Similar to the image in FIG. 5, the ultrasound images 510 in each of the screen captures in FIGS. 6A and 6B include a plurality of image elements (e.g., elements 512, 514, and 516), which may provide a graphical representation of a vector field (e.g., a vector flow image in element 512) and spatiotemporal information associated with the vector field (e.g., traces 532' and 533' of the velocity magnitude as a function of time and associated velocity angles represented by arrows 542' and 543' at the respective points 522' and 533'). Unlike the relatively laminar flow in FIG. 5 the flow at the carotid bulb is more turbulent as seen in the images in FIGS. 6A and 6B, and the variability in velocity magnitude and direction can be more easily perceived and quantified at specific selected point using the techniques described herein.

Figure 7:
FIGS. 7A, 7B, and 7C show additional examples of vector flow images generated using other VFI visualization techniques.

FIGS. 7A-7C illustrated different VFI imaging techniques which can be utilized for vector flow visualization by the systems described herein. While two dimensional (2D) vector fields are shown in the various illustrated examples herein, it will be understood that in some embodiments, the processor (e.g., vector flow processor 203) of the visualization and quantification system (e.g., system 200) may be configured to also estimate a third velocity component (e.g., elevational component) of the blood flow velocity in the ROI in addition to the axial and lateral components in order to produce a graphical representation of a three dimensional (3D) vector field (e.g., a 3D vector map). The 3D vector map may be overlaid on a 3D image of a volumetric ROI to provide a 3D rendering of the ultrasound data. In accordance with known techniques, slices may be taken through the imaged volumetric region and vector flow visualization and quantification may be performed at the selected image or slice plane and in some cases overlaid on the volume at the slice plane.

As described herein, one or more of the components of the system may be part of a stand-alone visualization system communicatively coupled to a source of ultrasonic imaging data, which may be pre-stored or received in real-time. For example, at least one of the display and the processor may be part of a workstation separate from the ultrasound imaging apparatus, and may be configured to generate the ultrasound image from real-time or pre-stored ultrasound imagining data. In further examples, the system for visualization and quantification according to the present disclosure may be integrated with an ultrasound imagining system configured to acquire the ultrasound echoes. For example, ultrasound imaging apparatus may be provided by an ultrasound diagnostic system including the display and the processor, wherein the ultrasound diagnostic system is configured to generate and update the ultrasound image in real time while ultrasonically imaging the subject.

Figure 8:
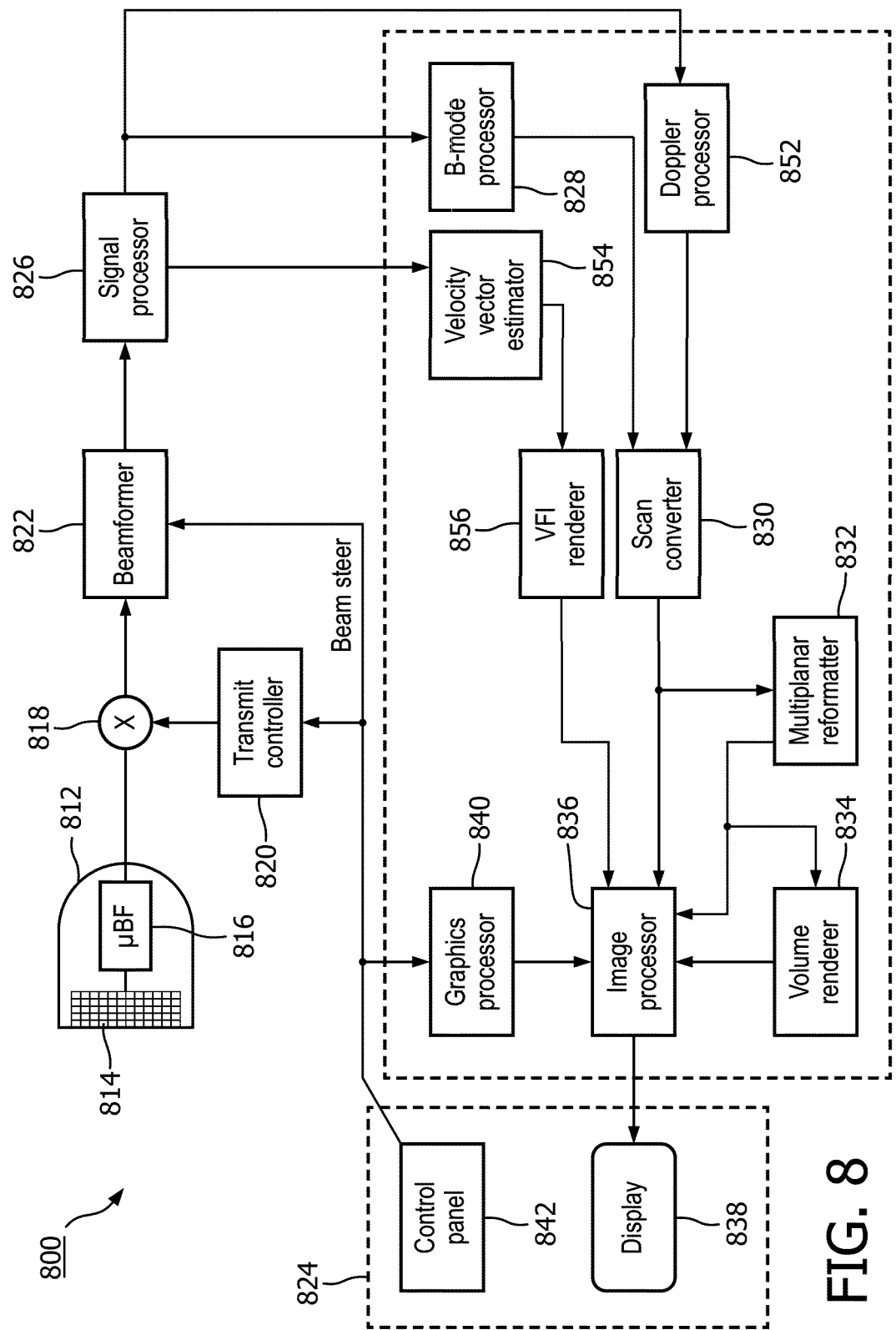
FIG. 8 shows a block diagram of an ultrasound imaging system in accordance with further examples of the present disclosure.

FIG. 8 shows a block diagram of an ultrasound system 800 according to the present disclosure. Some or all of the components of system 800 may be used to implement components of any one of the visualization and quantification systems described herein, for example the ultrasound imaging apparatus of FIG. 1. The ultrasound system 800 may include an ultrasound transducer array. In the illustrated example, the ultrasound transducer array 814 is provided in a probe 812. In some examples, the array 814 may be implemented using a plurality of patches, each comprising a sub-array of transducer elements and the array 814 may be configured to be conformably placed against the subject to be imaged. The array 814 is operable to transmit ultrasound toward a region of interest and to receive echoes for imaging the region of interest (ROI). A variety of transducer arrays may be used, e.g., linear arrays, curved arrays, or phased arrays. The array 814 may include, for example, a two dimensional array of transducer elements capable of scanning in both elevation and azimuth dimensions for 2D and/or 3D imaging.

The array 814 may be coupled to a microbeamformer, which may be located in the probe or in an ultrasound system base (e.g., in a cart-based system such as the SPARQ or EPIQ ultrasound system provided by Philips. The microbeamformer may control the transmission and reception of signals by the array. The array 814 may be coupled to the ultrasound system base via the microbeamformer 816, which may be coupled (via a wired or wireless connection) to a transmit/receive (T/R) switch 818 typically located in the base. The T/R switch 818 may be configured to switch between transmission and reception, e.g., to protect the main beamformer 822 from high energy transmit signals. In some embodiments, the functionality of the T/R switch 818 and other elements in the system may be incorporated within the probe, such as a probe operable to couple to a portable system, such as the LUMIFY system provided by PHILIPS. The probe 812 may be communicatively coupled to the base using a wired or wireless connection.

The transmission of ultrasonic pulses from the array 814 may be directed by the transmit controller 820 coupled to the T/R switch 818 and the beamformer 822, which may receive input from the user's operation of a user interface 824. The user interface 824 may include one or more input devices such as a control panel 842, which may include one or more mechanical controls (e.g., buttons, encoders, etc.), touch sensitive controls (e.g., a trackpad, a touchscreen, or the like), and other known input devices. Another function which may be controlled by the transmit controller 820 is the direction in which beams are steered. Beams may be steered straight ahead from (orthogonal to) the transmission side of the array 814, or at different angles for a wider field of view. The beamformer 822 may combine partially beamformed signals from groups of transducer elements of the individual patches into a fully beamformed signal. The beamformed signals may be coupled to a signal processor 826. The system 800 may include one or more processors (e.g., data and image processing components collectively referred to as 850) for generating ultrasound image data responsive to the echoes detected by the array 814, which may be provided in a system base. The processing circuitry may be implemented in software and hardware components including one or more CPUs, GPUs, and/or ASICs specially configured to perform the functions described herein for generating ultrasound images and providing a user interface for display of the ultrasound images.

For example, the system 800 may include a signal processor 826 which is configured to process the received echo signals in various ways, such as by bandpass filtering, decimation, I and Q component separation, and harmonic signal separation. The signal processor 826 may also perform additional signal enhancement such as speckle reduction, signal compounding, and noise elimination. The processed signals may be coupled to a B-mode processor 828 for producing B-mode image data. The B-mode processor can employ amplitude detection for the imaging of structures in the body. The signals produced by the B-mode processor 828 may be coupled to a scan converter 830 and a multiplanar reformatter 832. The scan converter 830 may be configured to arrange the echo signals in the spatial relationship from which they were received in a desired image format. For instance, the scan converter 830 may arrange the echo signal into a two dimensional (2D) sector-shaped format, or a pyramidal or otherwise shaped three dimensional (3D) format. The multiplanar reformatter 832 can convert echoes which are received from points in a common plane in a volumetric region of the body into an ultrasonic image (e.g., a B-mode image) of that plane, for example as described in U.S. Pat. No. 6,443,896 (Detmer). A volume renderer 834 may generate an image of the 3D dataset as viewed from a given reference point, e.g., as described in U.S. Pat. No. 6,530,885 (Entrekin et al.).

Additionally or optionally, signals from the signal processor 826 may be coupled to a Doppler processor 852, which may be configured to estimate the Doppler shift and generate Doppler image data. The Doppler image data may include colorflow data which may be overlaid with B-mode (or grayscale) image data for displaying a conventional duplex B-mode/Doppler image. In some examples, the Doppler processor 826 may include a Doppler estimator such as an auto-correlator, in which velocity (Doppler frequency) estimation is based on the argument of the lag-one autocorrelation function and Doppler power estimation is based on the magnitude of the lag-zero autocorrelation function. Motion can also be estimated by known phase-domain (for example, parametric frequency estimators such as MUSIC, ESPRIT, etc.) or time-domain (for example, cross-correlation) signal processing techniques. Other estimators related to the temporal or spatial distributions of velocity such as estimators of acceleration or temporal and/or spatial velocity derivatives can be used instead of or in addition to velocity estimators. In some examples, the velocity and power estimates may undergo threshold detection to reduce noise, as well as segmentation and post-processing such as filling and smoothing. The velocity and power estimates may then be mapped to a desired range of display colors in accordance with a color map. The color data, also referred to as Doppler image data, may then be coupled the scan converter 830 where the Doppler image data is converted to the desired image format and overlaid on the B-mode image of the tissue structure containing the blood flow to form a color Doppler image.

In accordance with the principles of the present disclosure, the system 800 may include vector flow processing components including a velocity vector estimator 854 and a VFI renderer 856. The velocity vector estimator may receive signals from the signal processor 826 and perform velocity estimation to obtain the angle-independent velocity vector data, as described herein. The velocity vector data (e.g., vector flow field) may be passed to a VFI renderer 856 for generating graphical representations of the velocity vector data, including vector field visualization data and spatiotemporal data. Output (e.g., images) from the scan converter 830, the multiplanar reformatter 832, the volume renderer 34, and/or the VFI renderer 856 may be coupled to an image processor 836 for further enhancement, buffering and temporary storage before being displayed on an image display 854. The system may include a graphics processor 840, which may generate graphic overlays for display with the images. These graphic overlays may contain, e.g., standard identifying information such as patient name, date and time of the image, imaging parameters, and other annotations. For these purposes, the graphics processor may be configured to receive input from the user interface 824, such as a typed patient name. Although shown as separate components, the functionality of any of the processors herein (e.g., the velocity vector estimator 854 and/or the VFI renderer 856) may be incorporated into other processors (e.g., image processor 836 or volume renderer 834) resulting in a single or fewer number of discrete processing units. Furthermore, while processing of the echo signals, e.g., for purposes of generating B-mode images or Doppler images are discussed with reference to a B-mode processor and a Doppler processor, it will be understood that the functions of these processors may be integrated into a single processor, which may be combined with the functionality of the vector flow processing components.

In various embodiments where components, systems and/or methods are implemented using a programmable device, such as a computer-based system or programmable logic, it should be appreciated that the above-described systems and methods can be implemented using any of various known or later developed programming languages, such as "C", "C++", "FORTRAN", "Pascal", "VHDL" and the like. Accordingly, various storage media, such as magnetic computer disks, optical disks, electronic memories and the like, can be prepared that can contain information that can direct a device, such as a computer, to implement the above-described systems and/or methods. Once an appropriate device has access to the information and programs contained on the storage media, the storage media can provide the information and programs to the device, thus enabling the device to perform functions of the systems and/or methods described herein. For example, if a computer disk containing appropriate materials, such as a source file, an object file, an executable file or the like, were provided to a computer, the computer could receive the information, appropriately configure itself and perform the functions of the various systems and methods outlined in the diagrams and flowcharts above to implement the various functions. That is, the computer could receive various portions of information from the disk relating to different elements of the above-described systems and/or methods, implement the individual systems and/or methods and coordinate the functions of the individual systems and/or methods described above.

In view of this disclosure it is noted that the various methods and devices described herein can be implemented in hardware, software and firmware. Further, the various methods and parameters are included by way of example only and not in any limiting sense. In view of this disclosure, those of ordinary skill in the art can implement the present teachings in determining their own techniques and needed equipment to affect these techniques, while remaining within the scope of the invention. The functionality of one or more of the processors described herein may be incorporated into a fewer number or a single processing unit (e.g., one or more CPUs or GPU) and may be implemented using application specific integrated circuits (ASICs) or general purpose processing circuits which are programmed responsive to executable instruction to perform the functions described herein.

Although the present system may have been described with particular reference to an ultrasound imaging system, it is also envisioned that the present system can be extended to other medical imaging systems where one or more images are obtained in a systematic manner. Accordingly, the present system may be used to obtain and/or record image information related to, but not limited to renal, testicular, breast, ovarian, uterine, thyroid, hepatic, lung, musculoskeletal, splenic, cardiac, arterial and vascular systems, as well as other imaging applications related to ultrasound-guided interventions. Further, the present system may also include one or more programs which may be used with conventional imaging systems so that they may provide features and advantages of the present system. Certain additional advantages and features of this disclosure may be apparent to those skilled in the art upon studying the disclosure, or may be experienced by persons employing the novel system and method of the present disclosure. Another advantage of the present systems and method may be that conventional medical image systems can be easily upgraded to incorporate the features and advantages of the present systems, devices, and methods.

Of course, it is to be appreciated that any one of the examples, embodiments or processes described herein may be combined with one or more other examples, embodiments and/or processes or be separated and/or performed amongst separate devices or device portions in accordance with the present systems, devices and methods.

Finally, the above-discussion is intended to be merely illustrative of the present system and should not be construed as limiting the appended claims to any particular embodiment or group of embodiments. Thus, while the present system has been described in particular detail with reference to exemplary embodiments, it should also be appreciated that numerous modifications and alternative embodiments may be devised by those having ordinary skill in the art without departing from the broader and intended spirit and scope of the present system as set forth in the claims that follow. Accordingly, the specification and drawings are to be regarded in an illustrative manner and are not intended to limit the scope of the appended claims.

What is claimed is:

1. A method for displaying ultrasound imaging data, the method comprising:
    generating with at least one processor an image from ultrasound data representative of a bodily structure and fluid flowing within the bodily structure;
    generating with the at least one processor, from the ultrasound data, vector field data corresponding to the fluid flow, wherein the vector field data comprises axial and lateral velocity components of the fluid;
    displaying, on a user interface, a graphical representation of the vector field data overlaid on the image;
    receiving, via the user interface, an indication of one or more user-selected points within the image;
    extracting, with the at least one processor, spatiotemporal information from the vector field data at the one or more user-selected points within the image; and
    concurrently displaying the spatiotemporal information at the one or more user-selected points with the image including the graphical representation of the vector field data, wherein the spatiotemporal information includes at least one of a magnitude and an angle of the fluid flow,
    wherein the displaying the spatiotemporal information includes displaying a visual representation of a direction of the fluid flow at the one or more user-selected points, wherein the visual representation of the direction of the fluid flow comprises a graph of a velocity vector plotting an axial component of the angle of the fluid flow versus a lateral component of the angle of the fluid flow at the one or more user-selected points, wherein the graph comprises a first axis representing the axial component, a second axis representing the lateral component, and an origin of the velocity vector is located at a position along the first axis and the second axis representing a zero value for the axial component and the lateral component, respectively, and
    wherein the graph of the velocity vector plotting the axial component of the angle of the fluid flow versus the lateral component of the angle of the fluid flow at the one or more user-selected points comprises a placeholder element that is populated with the velocity vector in response to receiving the indication of the one or more user-selected points within the image.

2. The method of claim 1, wherein the displaying the spatiotemporal information includes displaying a graph of the at least one of the magnitude and the angle of the fluid flow at the one or more user-selected points as a function of time.

3. The method of claim 1, wherein the visual representation is configured to dynamically update to reflect temporal changes in the direction of the fluid flow.

4. The method of claim 1, wherein the displaying the spatiotemporal information includes displaying information for the magnitude and the angle of the fluid flow, and wherein the displayed information for the magnitude and the angle of the fluid flow are synchronously updated in real-time responsive to the signals received from a region of interest (ROI) in a subject.

5. The method of claim 1, wherein the graphical representation of the vector field data is a pathlet-based graphical representation of the vector field.

6. The method of claim 1, wherein the graphical representation of the vector field data includes a vector map comprising a flow mask layer delineating a sub-region corresponding to the vector field data, and further comprising a vector visualization layer illustrating at least partial trajectories of velocity vectors in the sub-region.

7. The method of claim 1, further comprising estimating elevational velocity components of the fluid to obtain three dimensional (3D) vector field data for a volumetric region of interest (ROI).

8. The method of claim 7, wherein the concurrently displaying the spatiotemporal information at the one or more user-selected points with the image includes displaying a 3D image of the volumetric ROI overlaid with the 3D vector field data.

9. A system for visualization and quantification of ultrasound imaging data, the system comprising:
a display unit;
an input device configured to receive an input;
a processor communicatively coupled to the display unit and to an ultrasound imaging apparatus for generating an image from ultrasound data representative of a bodily structure and fluid flowing within the bodily structure, wherein the processor is configured to:
generate vector field data corresponding to the fluid flow, wherein the vector field data comprises axial and lateral velocity components of the fluid;
extract spatiotemporal information from the vector field data at one or more user-selected points within the image, wherein the one or more user-selected points within the image are indicated by the input received by the input device; and
cause the display unit to concurrently display the spatiotemporal information at the one or more user-selected points with the image including a graphical representation of the vector field data overlaid on the image, wherein the spatiotemporal information includes at least one of a magnitude and an angle of the fluid flow, wherein the display of the spatiotemporal information includes a visual representation of a direction of the fluid flow at the one or more user-selected points, wherein the visual representation of the direction of the fluid flow comprises a graph of a velocity vector plotting an axial component of the angle of the fluid flow versus a lateral component of the angle of the fluid flow at the one or more user-selected points, wherein the graph comprises a first axis representing the axial component, a second axis representing the lateral component, and an origin of the velocity vector is located at a position along the first axis and the second axis representing a zero value for the axial component and the lateral component, respectively, and wherein the graph of the velocity vector plotting the axial component of the angle of the fluid flow versus the lateral component of the angle of the fluid flow at the one or more user-selected points comprises a placeholder element that is populated with the velocity vector in response to the input received by the input device indicating the one or more user-selected points within the image.

10. The system of claim 9, wherein the ultrasound imaging apparatus is provided by an ultrasound diagnostic system including the display unit and the processor, and wherein the ultrasound diagnostic system is configured to generate and update the image in real-time while ultrasonically imaging the bodily structure.

11. The system of claim 9, wherein the processor is configured to generate a pathlet-based graphical representation of the vector field data.

12. The system of claim 9, wherein the graphical representation of the vector field data comprises a vector map including a flow mask layer defining a sub-region corresponding to the vector field data and a vector visualization layer illustrating at least partial trajectories of velocity vectors in the sub-region.

13. The system of claim 12, wherein the processor is configured to define the flow mask based on image segmentation, available vector field data, user input, or a combination thereof.

14. The system of claim 13, wherein the processor is configured to dynamically update the flow mask in subsequent image frames based on temporal variations of the available vector field data in corresponding vector flow frames.

15. The system of claim 9, wherein the processor is configured to cause the display unit to display, as the spatiotemporal information, a graph of the at least one of the magnitude and the angle of the fluid flow at the one or more user-selected points as a function of time.

16. The system of claim 9, wherein the visual representation is configured to dynamically update to reflect temporal changes in the direction of the fluid flow.

17. The system of claim 9, wherein the vector field data further comprises elevational velocity components of the fluid, and wherein the processor is configured to generate a three dimensional (3D) image of the ultrasound data overlaid with a graphical representation of a 3D velocity vector field.

18. The method of claim 1, further comprising acquiring the ultrasound data from a transducer array, a non-transitory computer readable medium, or a combination thereof.

* * * * *